(12) United States Patent
Mahesh et al.

(10) Patent No.: US 7,970,188 B2
(45) Date of Patent: Jun. 28, 2011

(54) SYSTEMS AND METHODS FOR AUTOMATIC ROUTING AND PRIORITIZATION OF EXAMS BASED ON IMAGE CLASSIFICATION

(75) Inventors: Prakash Mahesh, Hoffman Estates, IL (US); Mark Morita, Arlington Heights, IL (US); Murali Kumaran Kariathungal, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 938 days.

(21) Appl. No.: 11/562,826

(22) Filed: Nov. 22, 2006

(65) Prior Publication Data

US 2008/0118119 A1  May 22, 2008

(51) Int. Cl.
*G06K 9/00* (2006.01)
*G06K 9/62* (2006.01)
(52) U.S. Cl. ........................................ 382/128; 382/224
(58) Field of Classification Search .................. 382/128
See application file for complete search history.

(56) References Cited

U.S. PATENT DOCUMENTS

| | | | |
|---|---|---|---|
| 5,414,811 A | 5/1995 | Parulski et al. | |
| 6,148,301 A * | 11/2000 | Rosenthal | 707/10 |
| 6,173,275 B1 | 1/2001 | Caid et al. | |
| 6,493,703 B1 * | 12/2002 | Knight et al. | 707/3 |
| 6,640,001 B2 * | 10/2003 | Roehrig et al. | 382/128 |
| 6,760,714 B1 | 7/2004 | Caid et al. | |
| 2002/0016794 A1 * | 2/2002 | Keith, Jr. | 707/201 |
| 2003/0018802 A1 * | 1/2003 | Romanik et al. | 709/234 |
| 2004/0083257 A1 * | 4/2004 | Gortler et al. | 709/201 |
| 2004/0120558 A1 * | 6/2004 | Sabol et al. | 382/128 |
| 2004/0120580 A1 * | 6/2004 | Sabol et al. | 382/224 |
| 2004/0171955 A1 * | 9/2004 | Morganroth | 600/509 |
| 2004/0193413 A1 * | 9/2004 | Wilson et al. | 704/243 |
| 2005/0147284 A1 * | 7/2005 | Vining et al. | 382/128 |
| 2006/0104268 A1 * | 5/2006 | Lee et al. | 370/389 |
| 2006/0110035 A1 * | 5/2006 | Luo et al. | 382/170 |
| 2006/0110036 A1 * | 5/2006 | Luo et al. | 382/170 |

* cited by examiner

*Primary Examiner* — David P Zarka
(74) *Attorney, Agent, or Firm* — McAndrews, Held & Malloy, Ltd.; Michael A. Dellapenna

(57) ABSTRACT

Certain embodiments of the present invention provide a method for automatic prioritization and routing of exams for patients in a medical center based on image classification. The method includes capturing an image and digitizing it, automatically classifying the image based on its content, prioritizing the image based on its classification, and routing the image based on its prioritization and classification to the appropriate medical practitioner.

18 Claims, 3 Drawing Sheets

SYSTEMS AND METHODS FOR AUTOMATIC ROUTING AND PRIORITIZATION OF EXAMS BASED ON IMAGE CLASSIFICATION

BACKGROUND OF THE INVENTION

The present invention generally relates to medical exam prioritization and routing. In particular, the present invention relates to systems and methods for automatic routing and prioritization of exams based on image classification.

Medical practitioners, such as doctors, surgeons, and other medical professionals, often rely upon radiologists to read images of patients to determine where the patient should be routed for further medical care.

Over the last decade or so, acquisition of images for medical purposes has become widely digitized by using such devices as, for example, computed tomography (CT) scanners and magnetic resonance imaging (MRI) scanners. When the images are acquired, they are digitized, usually at the source (i.e., within the scanning device). After acquisition, the images are sent to a picture archiving communication system (PACS). The images can then be accessed from the PACS and displayed to radiologists who make assessments of the patient based on the images associated with him or her.

The number of radiology exams and size of studies are increasing in all types of hospitals and imaging centers. The number of radiologists is not increasing as to effectively accommodate this increase in the demand and use of radiology exams in diagnosis and routing of patients. As a result, there is tremendous pressure to increase the productivity of radiologists without affecting the quality of their work. This has become a very challenging issue in the medical field.

Existing systems and technologies are capable of providing images online upon demand and routing the images accordingly. However, many of these systems encounter problems as a result of creating work lists of the images based on body parts and modality types. The images are then accessed by radiologists according to their specialty. These systems do not take into account the criticality of the case and are not designed to make decisions as to who should read the exam based on the findings in the acquired images. The images often have computer-aided diagnosis (CAD) markings. Nevertheless, radiologists still have to examine the images to review the markings and decide to re-assign the exams to another radiologist based on the CAD findings.

Therefore, the main challenge encountered in the hospitals and radiology centers is that the volume of the images in a PACS is increasing, thereby increasing the demand for radiologists, but the number of radiologist is not increasing to accommodate this increase in volume. For example, in a busy hospital, on a given day, exams on the order of thousands are performed that involve imaging. Today, as a number of images for review is increasing, the number of available radiologists is decreasing, and, for a given radiologist, there is a greater amount of work to be done than in previous years. This may have such effects as delaying treatment to some patients especially those who may be in need of expedient care, and possibly misdiagnosing and routing patients to an erroneous destination.

Thus, there is a need for systems and methods for automatic routing and prioritizing of exams to specific destinations based on image classification.

BRIEF SUMMARY OF THE INVENTION

Certain embodiments of the present invention provide a method for automatic prioritization and routing of exams for patients in a medical center based on image classification. The method includes capturing an image and digitizing it, automatically classifying the image based on its content, prioritizing the image based on its classification, and routing the image based on its prioritization and classification to the appropriate medical practitioner.

Certain embodiments of the present invention provide a computer readable storage medium. The computer readable storage medium includes a set of instructions for execution on a computer. The set of instructions includes a capturing routine configured to capture an image set, a classifying routine configured to automatically classify and prioritize the image set, and a routing routine configured to automatically route the image set based on the classifying and prioritizing of the image set.

Certain embodiments of the present invention provide an image capturing device that captures an image set, and at least one processor that enables automatically classifying and prioritizing the image set. The at least one processor automatically routes the image set based on the classifying and prioritizing of the image set.

Figure 1:
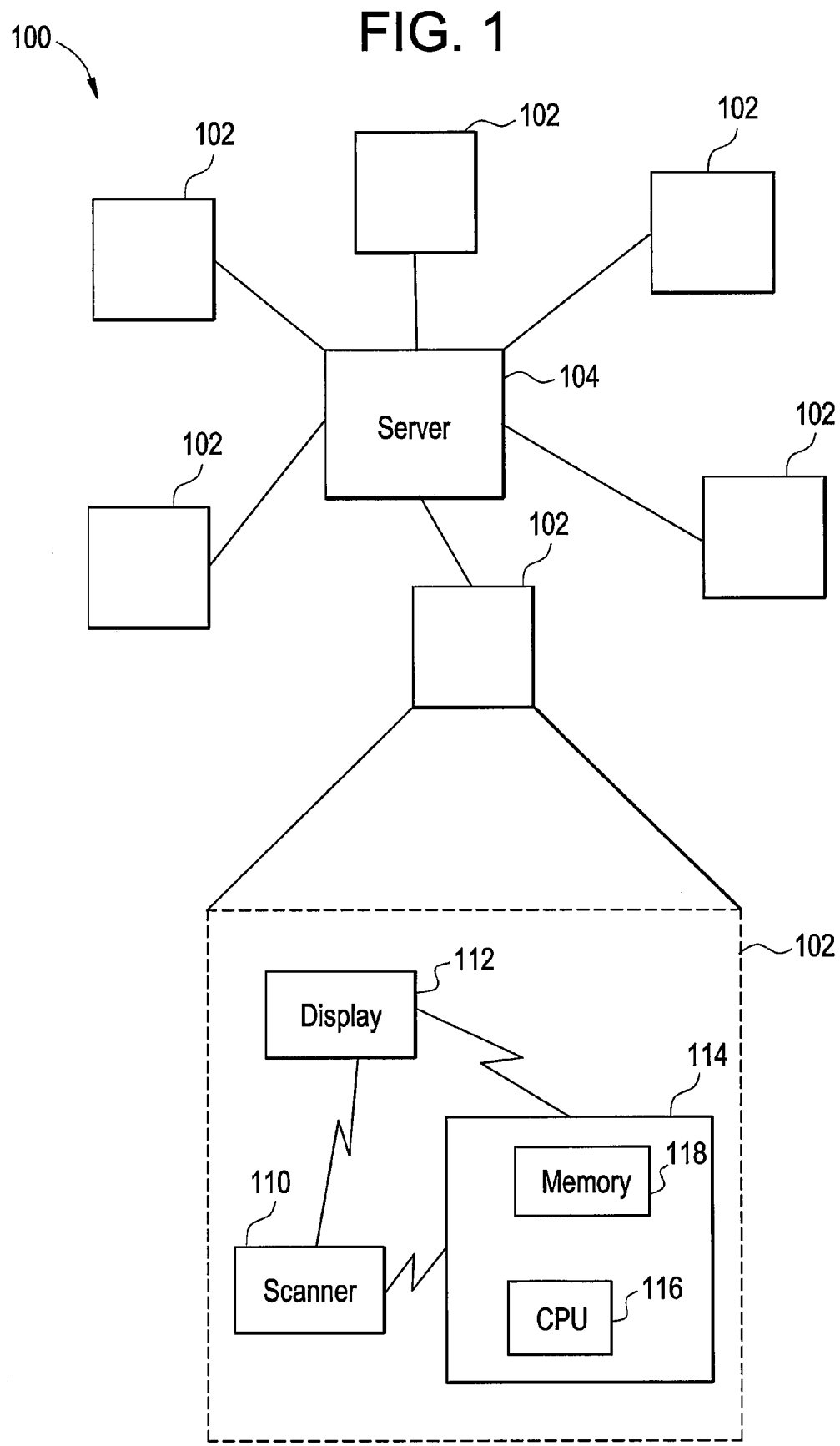
FIG. 1 illustrates a picture archiving communication system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Referring now to FIG. 1, an exemplary medical imaging system network is illustrated. The medical imaging system network 100 may be utilized in a medical center such as, for example, a hospital or a radiology center. The medical imaging system network 100 may include several image acquisition clients 102 communicatively coupled through a central server 104. Each of the image acquisition clients 102 may include an image acquisition device 110, a display device 112, and a computing and processing device 114, for example.

The image acquisition device 110 may be one of many devices used to capture medical images such as, for example, an ultrasound scanner, a magnetic resonance imaging (MRI) scanner, a positron emission tomography (PET) scanner, a computed tomography (CT) scanner, a X-ray scanner, etc. The image acquisition device 110 may capture images associated with a patient undergoing medical care. The image captured by the image acquisition device 110 may be transmitted to the computing and processing device 114 and displayed on the display device 112. The images captured by the image acquisition device 110 may be digitized in the computing and processing device 114 or in the image acquisition device 110. Information regarding the patient and image may be entered and stored in association with the digitized captured image.

The computing and processing device 114 may include hardware and/or software capable of processing the digitized captured images. The computing and processing device 114 may also include a processor 116 and memory 118. The computing and processing device 114 may process the captured images using image-processing techniques to determine the contents of the image. The contents of the digitized captured image may be processed along with the information regarding the associated patient, and the image may be classified based on the image contents. The classifications may be based on some input parameters. For example, the image may be classified according to its modality, i.e., whether the image is a CT, MRI, X-ray, PET scan, etc. Another exemplary classification may be the body part in the image such as, for example, the lungs, or kidneys, etc. Other classifications may indicate for example a disease or condition associated with the image and the body part in the image. The classification process may also determine the severity of the condition and assign a severity indicator to the image.

Based on the classification of the image, a set of rules may be retrieved from a rule database to further process the captured image. Each classification may have a set of rules associated with it. The set of rules is then applied in further processing of the captured image to assign a priority to each image based on the classifications associated with the image such as, for example, the severity of the condition of the patient and the medical specialty required for dealing with such a condition.

Based on the assigned prioritization, the image may be routed to a medical practitioner with the appropriate specialization to further care for the patient. The image and associated information may be sent and made available to a medical practitioner via the central server 104. The appropriate medical practitioner may access the cases and images assigned to him or her via any one of the image acquisition clients 102, connected to the central server 104.

The classifications may be programmed by the end user, for example, medical practitioners. Additionally, the rules may also be programmed by the end user, and may be changeable. For example, when a new radiologist or doctor joins the group of medical practitioners associated with the medical imaging system network 100, his information based on his specialty and experience may be added to the set of rules in the database and programmed to be associated with certain classifications.

In cases where the patient's condition may be critical such as when the patient was referred by a physician in the trauma center, a higher priority may be assigned to the patient's images. If based on the images it is determined that the patient's condition requires immediate attention, the referring physician may be notified immediately of the patient's condition.

Figure 2:
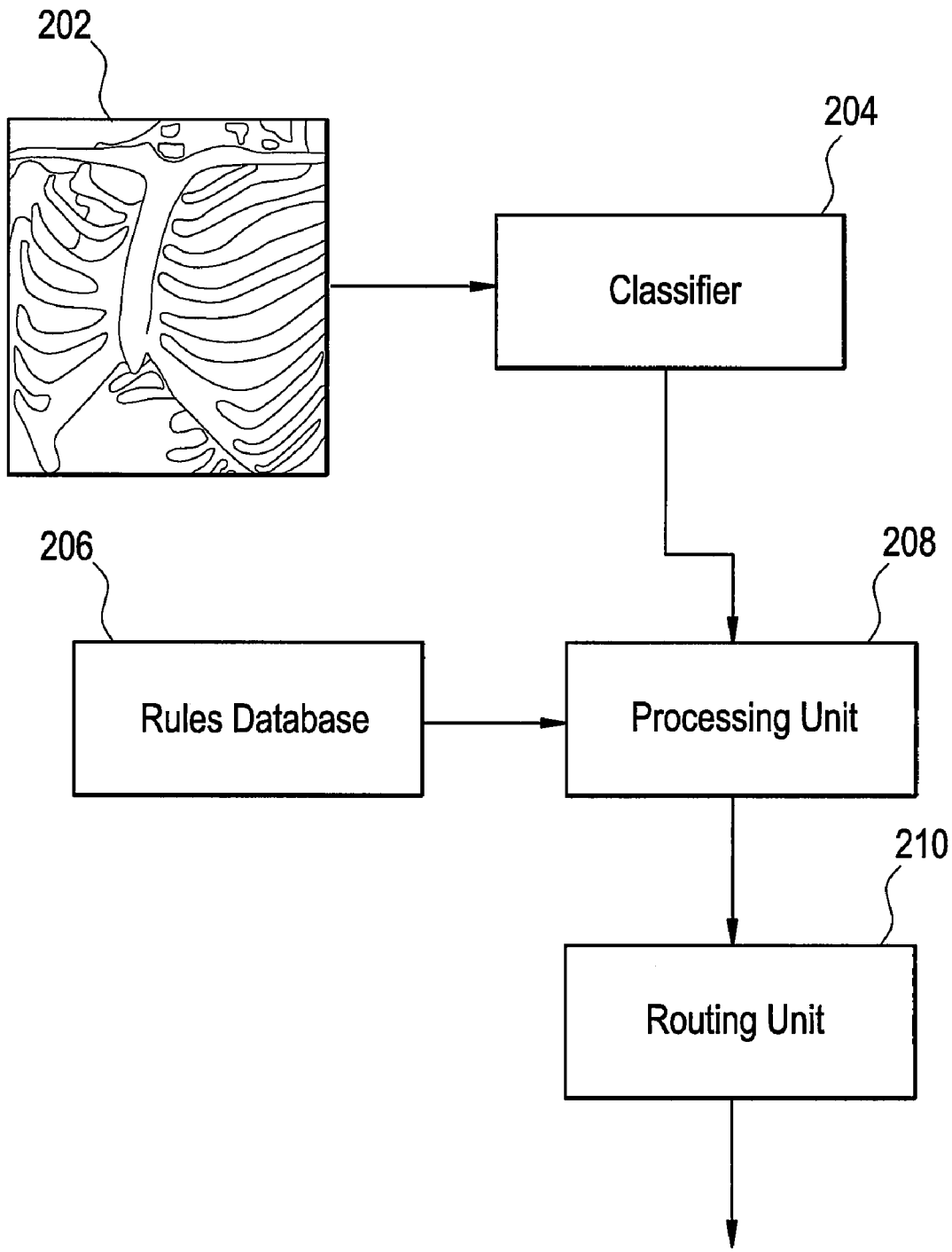
FIG. 2 illustrates a block diagram of an image prioritizing and routing system, in accordance with an embodiment of the present invention.

Referring now to FIG. 2, an exemplary block diagram of an image prioritizing and routing system 200 is illustrated. The image prioritizing and routing system 200 may include an image acquisition device 202, an image classifier 204, a rules database 206, a rules-processing unit 208, and a routing unit 210. The image prioritizing and routing system 200 may include hardware and/or software or a combination thereof.

The image acquisition device 202 may be one of many devices used to capture medical images such as, for example, an ultrasound scanner, a magnetic resonance imaging (MRI) scanner, a positron emission tomography (PET) scanner, a computed tomography (CT) scanner, a X-ray scanner, etc. The image acquisition device 202 may capture images associated with a patient undergoing medical care. The image captured by the image acquisition device 202 may be digitized and information regarding the patient and image may be transmitted with the captured image as header information.

The image classifier 204 may process the captured images to determine the contents of the image. The contents of the digitized captured image may be processed along with the information regarding the associated patient, and the image may be classified based on the image contents. The classifications may be based on some input parameters. For example, the image may be classified according to its modality, i.e., whether the image is a CT, MRI, X-ray, PET scan, etc. Another exemplary classification may be the body part in the image such as, for example, the lungs, or kidneys, etc. Other classifications may indicate for example a disease or condition associated with the image and the body part in the image. The classification process may also determine the severity of the condition and assign a severity indicator to the image.

Based on the classification of the image by the image classifier 204, a set of rules may be retrieved from the rule database 206 to further process the captured image. Each classification may have a set of rules associated with it. The set of rules retrieved from the rules database 206 may be then applied in the rules processing unit 208 to assign a priority to each image based on the classifications associated with the image such as, for example, the severity of the condition of the patient and the medical specialty required for dealing with such a condition.

Based on the assigned prioritization, the routing unit 210 may route the image to a medical practitioner with the appropriate specialization to further care for the patient. The image and associated information may be sent and made available to the appropriate medical practitioner. The appropriate medical practitioner may access the cases and images assigned to him or her.

The classifications may be programmed into the image classifier 204 by the end user, for example, medical practitioners. Additionally, the rules may also be programmed into the rules database 206 by the end user, and may be changeable. For example, when a new radiologist or doctor joins the group of medical practitioners associated with the image prioritizing and routing system 200, his information based on his specialty and experience may be added to the set of rules in the database and programmed to be associated with certain classifications.

Figure 3:
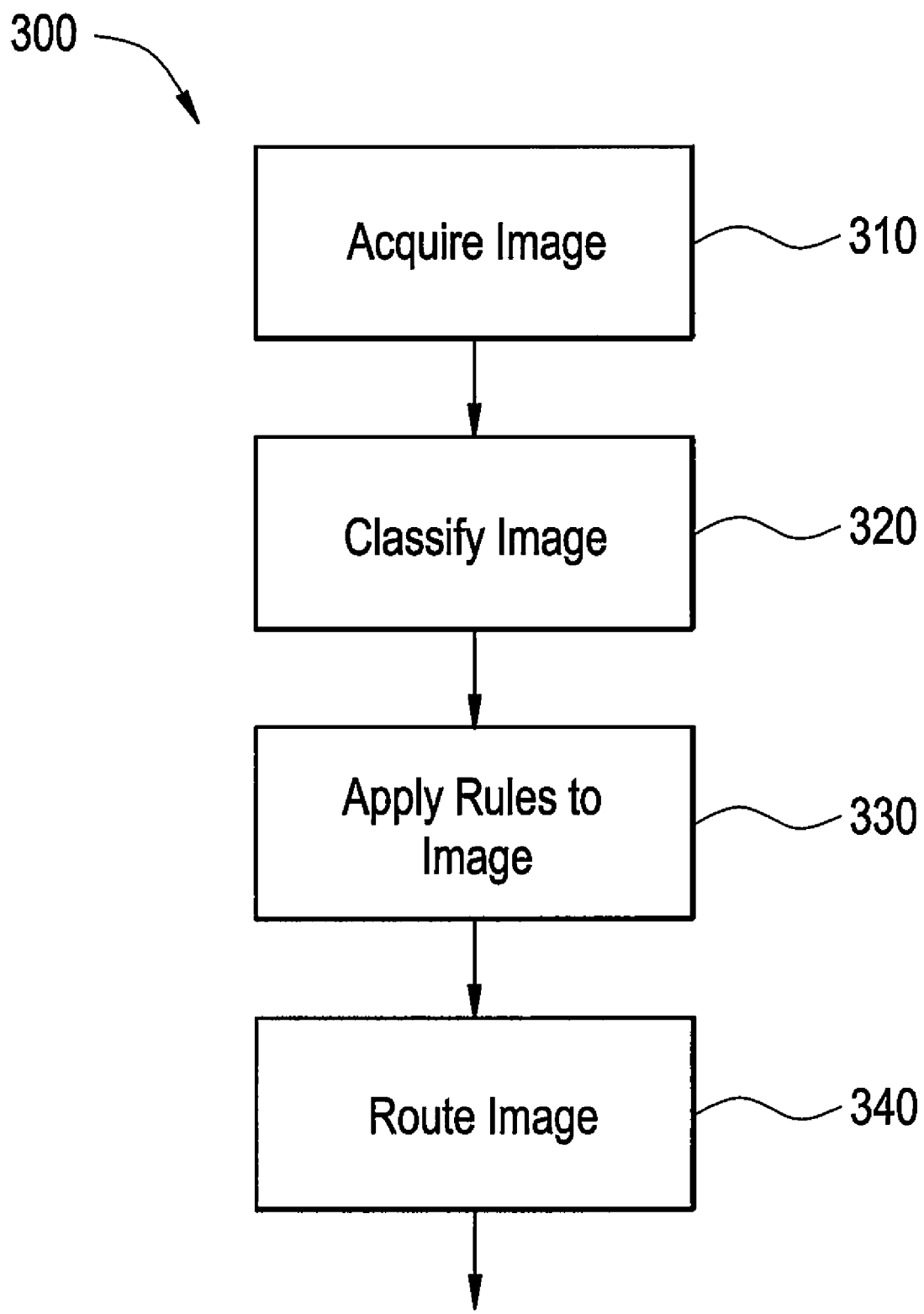
FIG. 3 illustrates a flowchart of a method for automatic prioritizing and routing system in accordance to an embodiment of the present invention.

FIG. 3 illustrates a flowchart of a method for automatic prioritizing and routing system in accordance to an embodiment of the present invention. The method 300 includes the following steps, which are described below in more detail. At step 310, an image set is acquired. At step 320, the image set is classified. At step 330, a set of rules is applied to the image set. At step 340, the image set is routed to an appropriate medical practitioner.

At step 310, an image set is acquired. The image set may include one or more images. The images may be acquired by one of many devices used to capture medical images such as, for example, an ultrasound scanner, a magnetic resonance imaging (MRI) scanner, a positron emission tomography (PET) scanner, a computed tomography (CT) scanner, a X-ray scanner, etc. The acquired images may be associated with a patient undergoing medical care. The captured images may be digitized and information regarding the patient and image may be included with the captured image as header information.

In certain embodiments of the present invention, information related to the patient, such as the position and orientation of the patient, may be associated with the image set. The patient information may be stored, for example, as header information in an image file.

At step 320, the image set may be classified. The image set may be processed to determine the contents of the image. The contents of the digitized captured image may be processed along with the information regarding the associated patient, and the image may be classified based on the image contents. The classifications may be based on some input parameters. For example, the image may be classified according to its modality, i.e., whether the image is a CT, MRI, X-ray, PET scan, etc. Another exemplary classification may be the body part in the image such as, for example, the lungs, or kidneys, etc. Other classifications may indicate for example a disease or condition associated with the image and the body part in the image. The classification process may also determine the severity of the condition and assign a severity indicator to the image.

At step 330, based on the classification of the images, a set of rules may be retrieved from a rule database and used to further process the captured image. Each classification may have a set of rules associated with it. The set of rules retrieved form the rules database may be then applied to the images to assign a priority to each image based on the classifications associated with the image such as, for example, the severity of the condition of the patient and the medical specialty required for dealing with such a condition.

At step 340, the image set may be routed to a medical practitioner based on the assigned prioritization. The medical practitioner may be one with the appropriate specialization to further care for the patient. The image and associated information may be sent and made available to the appropriate medical practitioner. The appropriate medical practitioner may access the images assigned to him or her and examine the images further to determine the appropriate approach to dealing with the patient and his particular condition.

The medical practitioners associated with the system may have several sub-specializations. In certain cases, it may be determined that more than one medical practitioner may be needed to examine a specific image set, in which case, the image set may be routed to all appropriate medical practitioners.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may include RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any medical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for automatic routing of exams based on image classification, the method comprising:
    determining a classification for an image that was acquired using a medical imaging device;
    using a computer processor to retrieve rules associated with the determined classification;
    using the computer processor to apply the retrieved rules to associate the image with a medical specialty and a medical condition severity;
    using the computer processor to compare the medical specialty and the medical condition severity to information in a data source to identify one or more medical practitioners that are associated with the medical specialty and the medical condition severity;
    using the computer processor to automatically route the image to the identified one or more medical practitioners; and
    using the computer processor to add medical practitioner information to the data source, the medical practitioner information including a medical practitioner identifier and an identification of the medical practitioner's associated medical specialty and medical condition severity.

2. The method of claim 1, wherein the classification of the image is automatically determined based at least in part on a modality of the medical imaging device used to acquire the image.

3. The method of claim 1, wherein the classification of the image is automatically determined based at least in part on a body part depicted in the image.

4. The method of claim 1, wherein the classification of the image is automatically determined based at least in part on a disease associated with the body part depicted in the image or a condition associated with the body part depicted in the image.

5. The method of claim 1, wherein the classification for the image is automatically determined using the computer processor.

6. The method of claim 1, further comprising acquiring the image using the medical imaging device.

7. A non-transitory computer readable storage medium including a set of instructions for execution on a computer, the set of instructions including:
    a first routine configured to retrieve rules associated with a classification determined for an image that was acquired using a medical imaging device;
    a second routine configured to apply the retrieved rules to associate the image with a medical specialty and a medical condition severity;
    a third routine configured to compare the medical specialty and the medical condition severity to information in a data source to identify one or more medical practitioners that are associated with the medical specialty and the medical condition severity
    a fourth routine configured to automatically route the image to the identified one or more medical practitioners; and
    a fifth routine configured to add medical practitioner information to the data source, the medical practitioner information including a medical practitioner identifier and an identification of the medical practitioner's associated medical specialty and medical condition severity.

8. The medium and instruction of claim 7, wherein the first routine is configured to automatically determine the classification for the image based at least in part on a modality of the medical imaging device used to acquire the image.

9. The medium and instruction of claim 7, wherein the first routine is configured to automatically determine the classification for the image based at least in part on a body part depicted in the image.

10. The medium and instruction of claim 7, wherein the first routine is configured to automatically determine the classification for the image based at least in part on a disease associated with the body part depicted in the image or a condition associated with the body part depicted in the image.

11. The medium and instruction of claim 7, wherein the first routine is configured to automatically determine the classification for the image.

12. The medium and instruction of claim 7, further comprising a fifth routine configured to acquire the image using the medical imaging device.

13. A system for automatic routing of exams based on image classification, the system comprising:
    a computer processor configured to receive an image that was acquired using a medical imaging device, the computer processor configured to retrieve rules associated with a classification determined for the image, the computer processor configured to apply the retrieved rules to associate the image with a medical specialty and a medical condition severity, the computer processor configured to compare the medical specialty and the medical condition severity to information in a data source to identify one or more medical practitioners that are associated with the medical specialty and the medical condition severity, the computer processor configured to automatically route the image to the identified one or more medical practitioners, and the computer processor configured to add medical practitioner information to the data source, the medical practitioner information including a medical practitioner identifier and an identification of the medical practitioner's associated medical specialty and medical condition severity.

14. The system of claim 13, wherein the computer processor is configured to automatically determine the classification for the image based at least in part on a modality of the medical imaging device used to acquire the image.

15. The system of claim 13, wherein the computer processor is configured to automatically determine the classification for the image based at least in part on a body part depicted in the image.

16. The system of claim 13, wherein the computer processor is configured to automatically determine the classification for the image based at least in part on a disease associated with the body part depicted in the image or a condition associated with the body part depicted in the image.

17. The system of claim 13, wherein the computer processor is configured to automatically determine the classification for the image.

18. The system of claim 13, further comprising an image capturing device that acquires the image using the medical imaging device.

* * * * *